US009482655B2

(12) United States Patent
Vilkov et al.

(10) Patent No.: US 9,482,655 B2
(45) Date of Patent: Nov. 1, 2016

(54) SYSTEM AND METHOD FOR USING ADDITIVES WITH ISOTOPIC PATTERNS TO ENHANCE THE SPECIFICITY OF A SPECTROMETER

(71) Applicant: MORPHO DETECTION, INC., Newark, CA (US)

(72) Inventors: Andrey N. Vilkov, Tustin, CA (US); Jack A. Syage, Corona del Mar, CA (US)

(73) Assignee: MORPHO DETECTION, LLC, Newark, CA (US)

( * ) Notice: Subject to any disclaimer, the term of this patent is extended or adjusted under 35 U.S.C. 154(b) by 379 days.

(21) Appl. No.: 14/133,921

(22) Filed: Dec. 19, 2013

(65) Prior Publication Data

US 2015/0177214 A1    Jun. 25, 2015

(51) Int. Cl.
*G01N 33/22* (2006.01)
*H01J 49/04* (2006.01)

(52) U.S. Cl.
CPC ............ *G01N 33/227* (2013.01); *H01J 49/04* (2013.01)

(58) Field of Classification Search
CPC .... G01N 33/227; G01N 33/22; G01N 33/00; Y10T 436/24; Y10T 436/00
USPC .............................. 436/173; 506/12, 7, 39, 33
See application file for complete search history.

(56) References Cited

U.S. PATENT DOCUMENTS

| 7,820,965 B2 | 10/2010 | Nagano et al. |
| 2009/0179147 A1* | 7/2009 | Milgram ............ G01N 30/8651 250/282 |
| 2010/0282962 A1 | 11/2010 | Nachuron-Mandard et al. |

OTHER PUBLICATIONS

Gao, S. et al, Sensitivity enhancement in liquid chromatography/atmospheric pressure ionization mass spectrometry using derivatization and mobile phase additives, Journal of Chromatography B, 825, 2005m 98-110.*
Shvartsburg, A. A. et al., "Isotopic Effect on Ion Mobility and Separation of Isotopomers by High-Field Ion Mobility Spectrometry," Anal Chem. Oct. 1, 2010; vol. 82; No. 19; pp. 8047-8051.
Ashcroft, A. E., "An Introduction to Mass Spectrometry," Astbury Centre for Structural Microbiology. (Mar. 3, 2009), retrieved from website http://www.astbury.leeds.ac.uk/facil/MStut/mstutorial.htm (19 pgs).

* cited by examiner

*Primary Examiner* — Christine T Mui
(74) *Attorney, Agent, or Firm* — Armstrong Teasdale LLP

(57) ABSTRACT

A method for detecting a chemical substance includes collecting a sample of a substance of interest and mixing the sample and at least one additive within a reaction chamber. The at least one additive includes a plurality of isotopes. The method also includes producing a plurality of adduct ions of the sample. The plurality of adduct ions has a plurality of isotopes. The method further includes performing a spectrometric analysis of the plurality of adduct ions and performing sample identification using comparative spectrometric data of the isotopes of the plurality of adduct ions.

28 Claims, 7 Drawing Sheets

SYSTEM AND METHOD FOR USING ADDITIVES WITH ISOTOPIC PATTERNS TO ENHANCE THE SPECIFICITY OF A SPECTROMETER

STATEMENT REGARDING FEDERALLY SPONSORED RESEARCH & DEVELOPMENT

This invention was made with Government support under contract number HSHQDC-10-C-00065 awarded by the Department of Homeland Security (DHS). The Government may have certain rights in this invention.

BACKGROUND OF THE INVENTION

The embodiments described herein relate generally to a trace detection technique for chemical substances, and, more particularly, to using additives with isotopic patterns to detect contraband substances such as explosives, narcotics, pesticides, and chemical warfare agents by means of high resolution mass spectrometry or ion mobility spectrometry.

In many known substance detection techniques, adduct ions are commonly used. Adducts are products of combining two or more distinct molecules to form a single product containing all of the atoms of all of the component molecules, thereby forming a distinct molecular species. Such distinct molecules may be positive or negative ions and the associated adduct ions are formed in either a positive ion mode or a negative ion mode, respectively, to enhance the sensitivity of spectrometry devices for certain classes of compounds of interest. The use of adducts facilitates ionization through ion attachment to only slightly ionizable or completely non-ionizable substances. Also, the use of adducts facilitates ionization through stabilizing fragile molecular ions which otherwise would fall apart during analysis thereby producing multiple fragments of substances of interest that may decrease the sensitivity to their detection. At least some of the known substance detection techniques include using such adducts as additives with dopants in both ion mobility spectrometry and mass spectrometry. Typical dopants used in trace detection of explosives are chlorinated compounds, e.g., in a negative ion mode, dichloromethane and chloroform, and, in positive ion modes, ammonia-based compounds, e.g., ammonia carbonate and anhydrous ammonia.

Some halogenated compounds such as chlorine and bromine have distinct natural isotopic patterns that are very useful for substance analysis. The natural distribution of isotopes, i.e., natural isotopic patterns for chlorine, e.g., $^{35}Cl$ and $^{37}Cl$, a difference of two neutrons, is about 3:1 and for bromine, i.e., $^{79}Br$ and $^{81}Br$, a difference of two neutrons, is about 1:1. The well-known rules of mass spectra interpretation facilitate using the associated isotopic patterns to determine the number of carbon, chlorine, and bromine atoms in a molecule of interest. Since the stable isotopes of common elements differ only by one or two neutrons, only high resolution mass spectrometry or ion mobility techniques may be appropriate for analysis of such isotopic patterns.

Known tandem mass spectrometry systems and methods currently play an almost exclusive role in the identification of chemical compounds of interest by means of mass spectrometry. In known tandem mass spectrometry methods, ions are typically fragmented by collisions with buffer gas molecules, and the fragmentation pattern is compared with the predetermined or calculated database of fragment ion masses. Such known tandem mass spectrometry methods are fairly successful in identifying substances of interest. However, such known tandem mass spectrometry systems are large, heavy, power intensive, and expensive. In addition, those trace detection systems that are the most attractive candidates due to size, weight, and power restrictions, e.g., single quadrupole mass spectrometry devices are not able to use tandem mass spectrometry methods for unambiguous identification of chemical substances.

BRIEF DESCRIPTION OF THE INVENTION

In one aspect, a method for detecting a chemical substance is provided. The method includes collecting a sample of a substance of interest and mixing the sample and at least one additive within a reaction chamber. The at least one additive includes a plurality of isotopes. The method also includes producing a plurality of adduct ions of the sample. The plurality of adduct ions has a plurality of isotopes. The method further includes performing a spectrometric analysis of the plurality of adduct ions and performing sample identification using comparative spectrometric data of the isotopes of the plurality of adduct ions.

In another aspect, a substance detection system is provided. The substance detection system includes a reaction chamber housing defining a reaction chamber therein. The system also includes a sample supply system coupled in flow communication with the reaction chamber. The sample supply system is configured to channel at least a portion of a sample of interest to the reaction chamber. The system further includes an additive system coupled in flow communication with the reaction chamber. The additive system is configured to channel at least one additive to the reaction chamber. The at least one additive includes a plurality of isotopes. The system also includes an ionization source coupled in flow communication with the reaction chamber. The ionization source is configured to produce a plurality of isotopic adduct ions from the at least a portion of the sample of interest and the at least one additive including the plurality of isotopes. The system further includes a spectrometric analysis device coupled in flow communication with the reaction chamber. The spectrometric analysis device is configured to perform a spectrometric analysis of the plurality of isotopic adduct ions. The system also includes a processor configured to identify at least one substance of interest using comparative spectrometric data of the plurality of isotopic adduct ions.

BRIEF DESCRIPTION OF THE DRAWINGS

FIG. 1 is a schematic view of an exemplary substance detection system;

FIG. 2 is an exemplary method of using additives with isotopic patterns to detect substances of interest using the substance detection system shown in FIG. 1;

FIG. 3 is a graphical view of an exemplary mass spectrum of NG-Cl and NG-Br adduct ions acquired in a negative mode, in which the first pair of adduct ions is $[NG+^{35,37}Cl]^-$ and the second pair is $[NG+^{79,81}Br]^-$, using the substance detection system shown in FIG. 1 and the method shown in FIG. 2;

FIG. 4 is a graphical view an exemplary mass spectrum of triacetone triperoxide (TATP)-ammonia adduct ions in a positive mode, where ammonia adducts are equally split between $^{14}NH_4$ and $^{15}NH_4$ isotopes, obtained using the substance detection system shown in FIG. 1 and the method shown in FIG. 2;

FIG. 5 is a graphical view of four thermal desorption profiles corresponding to $[NG+^{35,37}Cl]^-$ and $[NG+^{79,81}Br]^-$ adduct ions;

FIG. 6 is a graphical view of exemplary thermal desorption profiles corresponding to $[M+^{35,37}Cl]^-$ and other ionic compounds $[N]^-$ and $[N+2]^-$; and FIG. 7 is a graphical view of exemplary chromatographic profiles corresponding to $[M+^{35,37}Cl]^-$ and other ionic compounds $[N]^-$ and $[N+2]^-$.

DETAILED DESCRIPTION OF THE INVENTION

The embodiments described herein enhance the specificity of trace detection systems through the use of additives having distinct isotopic patterns with a propensity to form predetermined adduct ions with substances of interest. Use of compounds with known, naturally-occurring isotopic distributions increases the specificity of identification in a cost-effective manner. Specifically, the embodiments described herein facilitate use of smaller, lighter, lower power intensive, and less expensive spectrometric analysis devices, e.g., single quadrupole mass spectrometry devices. Greater levels of specificity are attained if a mix of additives with different isotopic distributions is used. For example, use of chlorine and bromine together produce molecular ions with both chlorine and bromine adducts and each pair of ions have their own isotopic distribution. Furthermore, adduct ions are formed by attachment of a single additive molecular ion as well as multiple additive ions, for example two isotopic chlorine ions or one ion each of isotopic chlorine and bromine. In such cases, the isotopic patterns are even more complex, and thus more distinctive. In addition, additives that produce ions other than adduct ions generate useful information on isotopic patterns, e.g., adducts may be formed with fragment ions of substances of interest or adduct ions may fall apart forming fragment adduct ions. Furthermore, rather than use naturally-occurring isotopic distributions, use of artificially isotopically-enriched compounds facilitates generating distinct isotopic patterns with even greater specificity.

Figure 1:
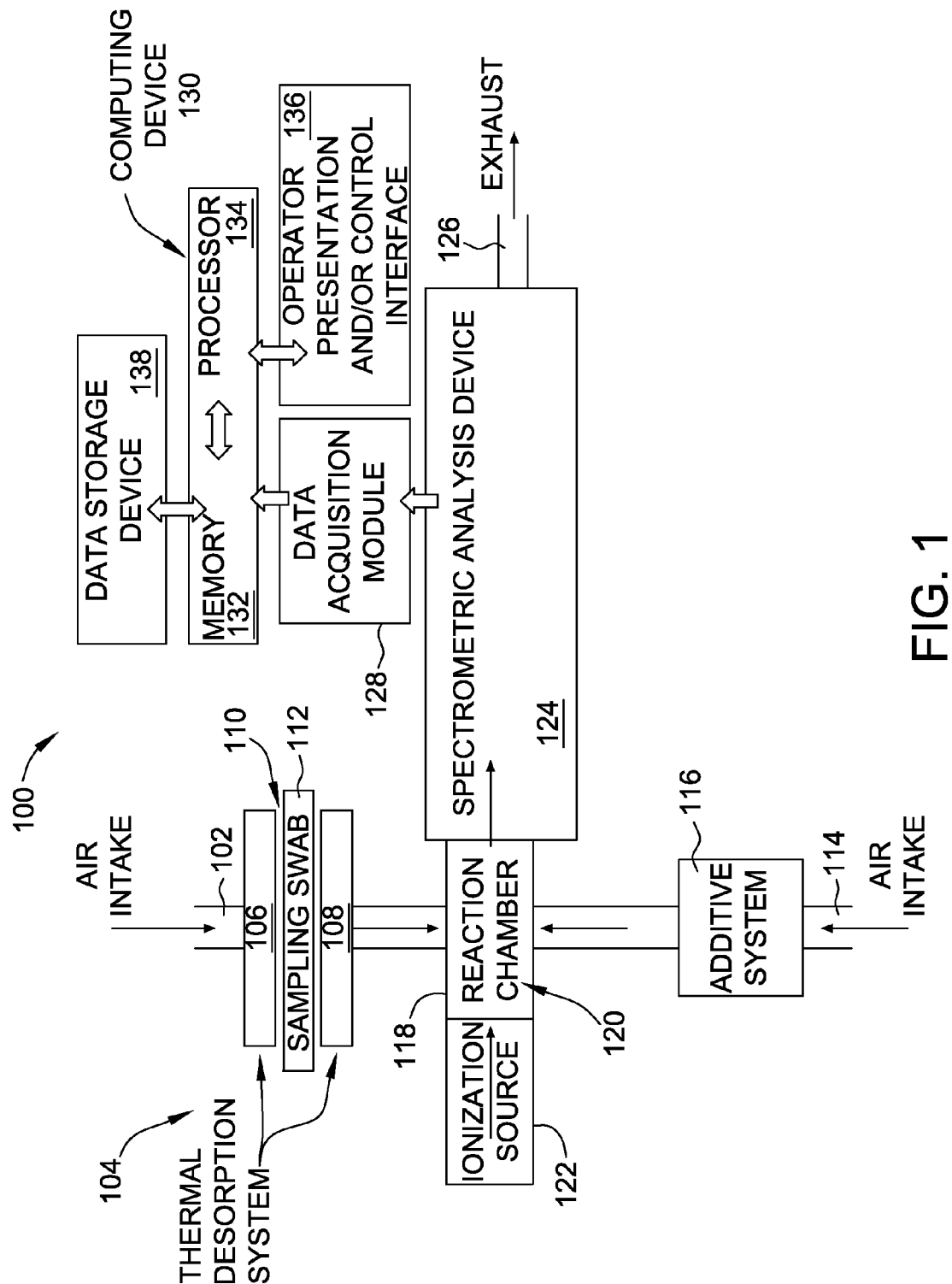
FIGS. 1-7 show exemplary embodiments of the systems and methods described herein.

FIG. 1 is a schematic view of an exemplary substance detection system 100. System 100 includes a first air intake device 102. System 100 also includes a sample supply system, i.e., in the exemplary embodiment, a thermal desorption system 104 coupled in flow communication with first air intake device 102. Thermal desorption system 104 includes a first heating device 106 and a second heating device 108 that define a sampling swab insertion port 110 that receives sampling swabs 112. Alternatively, any configuration of thermal desorption system 104 than enables operation of system 100 as described herein is used. Substance detection system 100 further includes a second air intake device 114. System 100 also includes an additive system 116 coupled in flow communication with second air intake device 114. System 100 further includes a reaction chamber housing 118 defining a reaction chamber 120 coupled in flow communication with thermal desorption system 104 and additive system 116.

Substance detection system 100 also includes an ionization source 122 coupled in flow communication with reaction chamber 120. Ionization source 122 is any ionization system that enables operation of system 100 as described herein, including, without limitation, a radioactive ionization source, an electrospray ionization source (ESI), an atmospheric pressure chemical ionization (APCI) source, an atmospheric pressure photoionization (APPI) source, an atmospheric pressure glow discharge (APGD) source, and an atmospheric pressure dielectric barrier discharge (APDBD) source. Some embodiments of substance detection system 100 are configured to operate at sub-atmospheric pressures. Such embodiments include an ionization source 122 that is, e.g., and without limitation, a chemical ionization (CI) source, a photoionization (PI) source, a glow discharge (GD) source, and a dielectric barrier discharge (DBD) source.

Substance detection system 100 further includes a spectrometric analysis device 124 coupled in flow communication reaction chamber 120. In the exemplary embodiment, spectrometric analysis device 124 is a single quadrupole mass spectrometry device. Alternatively, spectrometric analysis device 124 is any spectrometric analysis system that enables operation of system 100 as described herein, including, without limitation, any mass spectrometry device, any ion mobility spectrometry device, and any differential ion mobility spectrometry device. System 100 also includes an exhaust device 126 coupled in flow communication with spectrometric analysis device 124.

Substance detection system 100 also includes a data acquisition module 128 coupled to spectrometric analysis device 124. System 100 further includes a computing device 130 coupled to data acquisition module 128. In the exemplary embodiment, computing device 130 is used to perform spectrometric analyses of the spectrum data imported from data acquisition module 128. Alternatively, computing device 130 also facilitates control of spectrometric analysis device 124, data acquisition module 128, and any other apparatus associated with substance detection system 100.

As used herein, the term "computer" and related terms, e.g., "computing device", are not limited to integrated circuits referred to in the art as a computer, but broadly refers to a microcontroller, a microcomputer, a programmable logic controller (PLC), an application specific integrated circuit, and other programmable circuits, and these terms are used interchangeably herein. Further, as used herein, the terms "software" and "firmware" are interchangeable, and include any computer program stored in memory for execution by personal computers, workstations, clients and servers.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

Computing device 130 includes a memory device 132 and a processor 134 operatively coupled to memory device 132 for executing instructions. In some embodiments, executable instructions are stored in memory device 132. Computing device 130 is configurable to perform one or more operations described herein by programming processor 134. For example, processor 134 may be programmed by encoding an operation as one or more executable instructions and providing the executable instructions in memory device 132. In the exemplary embodiment, memory device 132 is one or more devices that enable storage and retrieval of information such as executable instructions and/or other data. Memory device 132 may include one or more computer readable media.

Memory device 132 may be configured to store operational measurements including, without limitation, real-time and historical spectrometric data including, without limitation, sample identification using comparative spectrometric data, isotopic ratios of molecular adduct ions and fragment adduct ions, timing data of elution profiles, thermal desorption profiles, and chromatographic elution profiles for isotopes of adduct ions, and data on ratios of isotopic adduct ions, e.g., relative intensities of isotopic peaks and peak areas of adduct ions in a spectrum, and/or any other type data.

As used herein, the term "real-time" refers to at least one of the time of occurrence of the associated events, the time of measurement and collection of predetermined data, the time to process the data, and the time of a system response to the events and the environment. In the embodiments described herein, these activities and events occur substantially instantaneously.

Computing device 130, including memory device 132, includes, without limitation, sufficient computer-readable/executable instructions, sufficient data and data structures, algorithms, and commands to facilitate generating comparisons of the data imported from data acquisition module 128 with the stored historical spectrometric data described above. In addition, computing device 130 either includes, or is coupled to, a data storage device 138 that is configured to store such computer-readable/executable instructions, historical data and data structures, algorithms, and commands.

Substance detection system 100 further includes an operator presentation and/or control interface 136 coupled to computing device 130. Interface 136 presents data, such as spectrometric comparison data to a user (not shown). In some embodiments, interface 136 includes one or more display devices. In some embodiments, interface 136 presents an audible and/or graphical notification upon detection of a substance of interest. Also, in some embodiments, interface 136 facilitates control of computing device 130 and manual data input into computing device 130. Furthermore, in some embodiments, computing device 130 is coupled in communication with one or more other devices, such as another computing device 130, locally or remotely. As such, substance detection system 100 may be networked with other systems and devices such that data transmitted across portions of system 100 may be accessed by any device capable of accessing computing device 130 including, without limitation, desktop computers, laptop computers, and personal digital assistants (PDAs) (neither shown).

Figure 2:
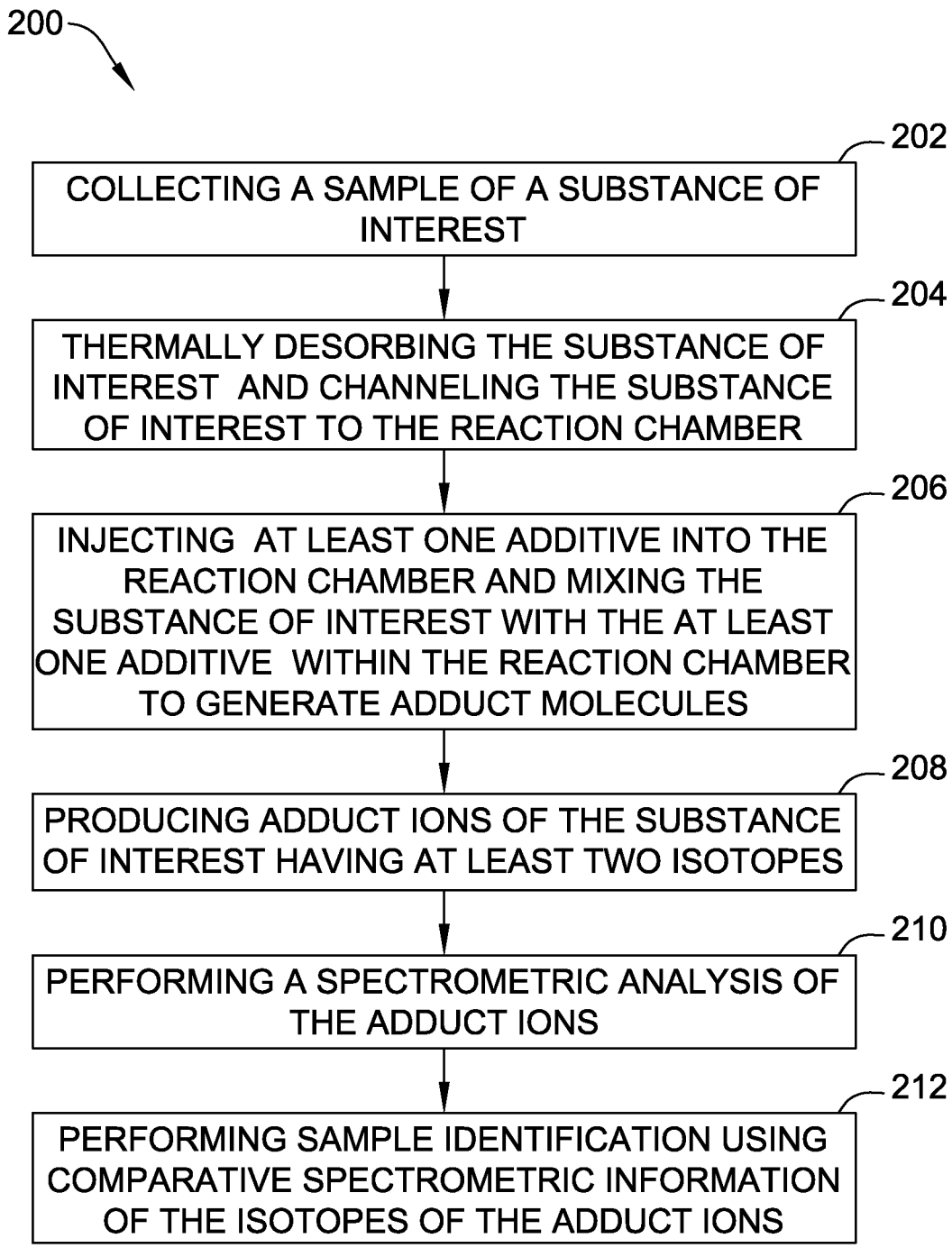

FIG. 2 is an exemplary method 200 of using additives with isotopic patterns to detect substances of interest using substance detection system 100 (shown in FIG. 1). In the exemplary embodiment, a fresh sampling swab 112 (shown in FIG. 1) is used to wipe a surface of interest (not shown) to collect 202 a sample of a substance, or substances, of interest. Such substances of interest include, without limitation, triacetone triperoxide (TATP), ethylene glycol dinitrate (EGDN), nitroglycerin (NG), Research Department Explosive (RDX), pentaerythritol tetranitrate (PETN), high melting explosive (HMX), and urea nitrate (UN). Sampling swab 112 is inserted into sampling swab insertion port 110 (shown in FIG. 1).

Method 200 also includes thermally desorbing 204 the substances of interest and channeling those substances to reaction chamber 120 (shown in FIG. 1). Air is pulled into thermal desorption system 104 through first air intake 102 and first heating device 106 and a second heating device 108 are energized to heat up and desorb the substances from sampling swab 112. The desorbed substances are entrained in the air flow and are channeled to reaction chamber 120 for ionization.

Method 200 further includes injecting 206 at least one additive into reaction chamber 120 and mixing the sample of the substance of interest with at least one additive within reaction chamber 120, thereby generating adduct molecules. In the exemplary embodiment, at least one additive has at least two isotopes. Such additives are channeled from additive system 116 (shown in FIG. 1) through air pulled into system 100 through second air intake 114 (shown in FIG. 1). Certain dopants may also be injected into reaction chamber 120 through additive system 116 with the other additives, e.g., without limitation, ammonium ($NH_4$) and nitrates ($NO_3$).

A first category of such additives to produce distinct isotopic patterns includes halogenated compounds, e.g., and without limitation, additive molecules that includes chlorine molecules and bromine molecules with distinct natural isotopic distributions that include $^{35}Cl$ and $^{37}Cl$ isotopes and $^{79}Br$ and $^{81}Br$ isotopes, respectively. Chloride ($Cl^-$) and bromide ($Br^-$) ions react with a large variety of commercial, military, and homemade explosives such as EGDN, NG, RDX, PETN, HMX, UN, and Tetryl, thereby forming chloride-adduct ions and bromide-adduct ions in a negative ion mode.

A second category of such additives to produce distinct isotopic patterns is to use a mix of naturally, almost mono-isotopic additives with their isotopically-enriched counterparts. As used herein, the term "almost mono-isotopic" refers to an additive that includes a plurality of naturally-occurring isotopes where one of the isotopes is greater than approximately 90% of the natural abundance of the total number of molecules in the naturally-occurring additive. For example, nitrogen (N) has two naturally occurring isotopes, i.e., a $^{14}N$ isotope and a $^{15}N$ isotope, where the natural abundance of the $^{14}N$ isotope is greater than 99% and the abundance of the $^{15}N$ isotope is less than 1%. Therefore, the $^{15}N$ isotope may be used in a mixture with the $^{14}N$ isotope in such dopants as $NH_4$ and $NO_3$. As such, the use of artificially isotopically-enriched compounds facilitates producing substantially variable, and at least partially arbitrary, isotopic ratios of the $^{14}N$ isotope to the $^{15}N$ isotope that are enhanced to ratios such as, and without limitation, 5:1 and 7:1. Subsequently, a mixture of $^{14}NH_4$ and $^{15}NH_4$ in a gaseous phase may be used as an additive for detection of explosives such as TATP and UN as well as a variety of pesticides in a positive ion mode through forming ammonium-adduct ions. In addition, a mixture of $^{14}NO_3$ and $^{15}NO_3$ in a gaseous phase may be used as an alternative to common chlorine-containing dopants typically used in the detection of a variety of explosives such as EGDN, NG, RDX, PETN, HMX, UN, and Tetryl, thereby forming nitrate-adduct ions in a negative ion mode.

Similar artificial isotopical enrichment may also be performed for those additives that include molecules of, without limitation, $^{17}O$ isotope, $^{18}O$ isotope. $^{2}H$ isotope, $^{13}C$ isotope, and $^{41}K$ isotope.

Method 200 also includes producing 208 adduct ions of the sample of the substance of interest having at least two isotopes. The adduct ions may have either a negative polarity in the negative ion mode or a positive polarity in the positive ion mode. As described above, for each of the two polarities, the isotopic additives and the sample of the substance of interest are mixed in reaction chamber 120, thereby forming adducts, i.e., molecules of the additive and molecules of the sample from combined molecules of additive and sample. Ionization source 122 ionizes each of the isotopes now embedded within these adducts. For example, in the negative ion mode, with the ions generated having a negative polarity, the ionized $^{35}Cl$ and $^{37}Cl$ isotopes and $^{79}Br$ and $^{81}Br$ isotopes, in combination, generate a distinct pattern. Since these halogenated compounds react with explosives that do not ionize well such as EGDN, NG, RDX, PETN, HMX, and UN, the ionized isotopes enhance the sensitivity of spectrometric analysis device 124 to determine the presence of substances of interest in the sample being analyzed.

Method 200 further includes performing 210 a spectrometric analysis of the adduct ions. The adduct ions are channeled from reaction chamber 120 into spectrometric analysis device 124 for generating the associated graphical representations of the determined mass spectrums.

Method 200 also includes performing 212 sample identification using comparative spectrometric data of the isotopes of the adduct ions.

Figure 3:
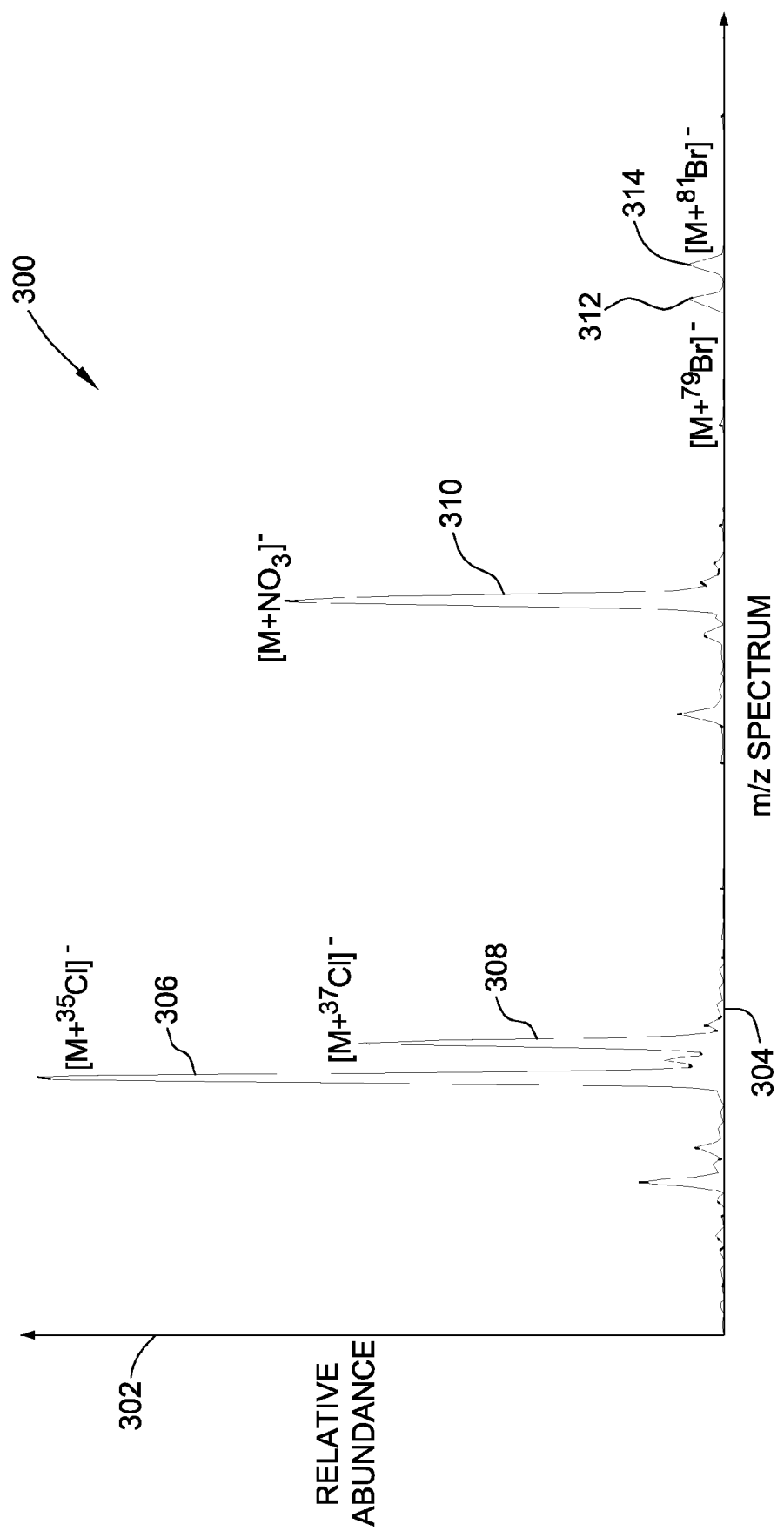

FIG. 3 is a graphical view, i.e., plot 300 of an exemplary mass spectrum of NG-Cl and NG-Br adduct ions acquired in a negative ion mode, in which the first pair of adduct ions is $NG+^{35,37}Cl$ and the second pair is $NG+^{79,81}Br$, using substance detection system 100 (shown in FIG. 1) and method 200 (shown in FIG. 2). In general, injecting 206 (shown in FIG. 2) isotopic additives with natural distributions such as chlorine with the naturally-occurring isotopes $^{35}Cl$ and $^{37}Cl$ into reaction chamber 120 to mix with a thermally desorbed 204 (shown in FIG. 2) sample of a substance of interest (M) produces ionized adducts $[M+^{35}Cl]^-$ and $[M+^{37}Cl]^-$. Similarly, using bromine with the naturally-occurring isotopes $^{79}Br$ and $^{81}Br$, ionized adducts $[M+^{79}Br]^-$ and $[M+^{81}Br]^-$. Using ionization source 122 (shown in FIG. 1) to produce 208 (shown in FIG. 2) negatively-charged adduct ions $[M+^{35}Cl]^-$, $[M+^{37}Cl]^-$, $[M+^{79}Br]^-$, and $[M+^{81}Br]^-$ increases the specificity of identifying the substance of interest M after performing 210 (shown in FIG. 2) a spectrometric analysis and sample identification analysis 212 (shown in FIG. 2). In the exemplary embodiment, the substance of interest M is nitroglycerin (NG).

Plot 300 includes a y-axis 302 representative of the relative abundances of the ionized molecules. Y-axis 302 is non-numerical to illustrate the approximate ionic abundances relative to each other. Plot 300 also includes an x-axis 304 representative of the spectrum of the mass-to-charge (m/z) ratios of the ionic molecules, where m is the value of the atomic mass unit, e.g., 35, 37, 79, and 81, and z is the ionic charge, e.g., 1, 2, and 3. Plot 300 shows five significant peaks of interest. First peak 306 represents the relative abundance of the ionic adduct $[NG+^{35}Cl]^-$. Second peak 308 represents the relative abundance of the ionic adduct $[NG+^{37}Cl]^-$. Third peak 310 represents the relative abundance of the molecular ionic adduct $[NG+NO_3]^-$ since a nitrate dopant $NO_3$ was also injected into reaction chamber 120 through additive system 116 with the chlorine and bromine additives. Such dopants further enhance the specificity of identification of substances M. Fourth peak 312 represents the relative abundance of the ionic adduct $[NG+^{79}Br]^-$ and fifth peak 314 represents the relative abundance of the ionic adduct $[NG+^{81}Br]^-$.

Referring again to FIG. 2, as well as FIG. 3, as associated with performing 212 sample identification using comparative spectrometric data of the isotopes of the adduct ions, plot 300 may be representative of the real-time data imported into computing device 130 from data acquisition module 128 or historical spectrometric data resident in storage device 138 (all shown in FIG. 1).

In some embodiments, sample identification is performed 212 using comparative spectrometric data such as comparing ratios of associated isotopic adduct ions. In the exemplary embodiment, two ratio comparisons include comparing the values of relative peak intensity values (y-axis 302) of peaks 306, 308, 312, and 314 to each other and/or to historical data and comparing the isotopic peak areas defined by each of peaks 306, 308, 312, and 314 to each other and/or to historical data.

A third ratio comparison includes comparing ratios of associated isotopic adduct ions as defined by peaks 306, 308, 312, and 314 to isotopic ratios of molecular adduct ions such as third peak 310 representing the relative abundance of the molecular ionic adduct $[NG+NO_3]^-$, including real-time data and/or historical data.

A fourth ratio comparison includes comparing isotopic ratios of fragment adduct ions including real-time data and/or historical data. The use of adducts facilitates ionization through stabilizing fragile molecular ions which otherwise would fall apart during analysis thereby producing multiple fragments of substances of interest that may decrease the sensitivity to their detection. However, some ions may be fragmented, and not only molecular adduct ions can bear useful data within the isotopic patterns, but also adducts may be formed with fragment ions of substance of interest or molecular adduct ion may fall apart forming fragment adduct ions. The recorded fragmentation pattern is compared with the predetermined or calculated database of fragment ion masses.

Figure 4:
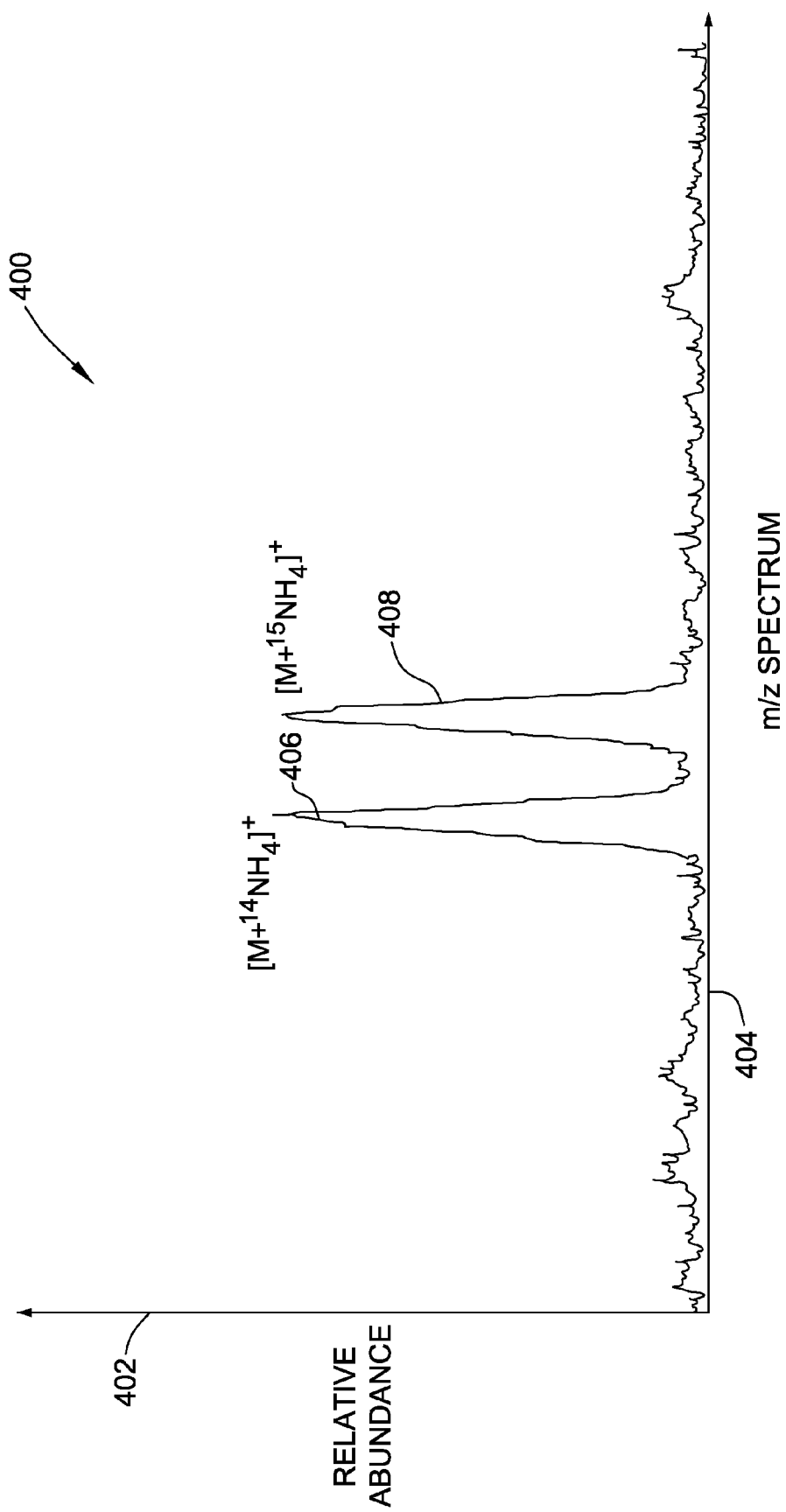

FIG. 4 is a graphical view, i.e., plot 400 of an exemplary mass spectrum of triacetone triperoxide (TATP)-ammonia adduct ions in a positive mode, where ammonia adducts are equally split between $^{14}NH_4$ and $^{15}NH_4$ isotopes of nitrogen, obtained using substance detection system 100 (shown in FIG. 1) and method 200 (shown in FIG. 2). In the exemplary embodiment, the substance of interest M is TATP. Plot 400 includes a y-axis 402 representative of the relative abundances of the ionized molecules. Y-axis 402 is non-numerical to illustrate the approximate ionic abundances relative to each other. Plot 400 also includes an x-axis 404 representative of the spectrum of the mass-to-charge (m/z) ratios of the ionic molecules. Plot 400 shows two significant peaks of interest. The first peak 406 represents the relative abundance of the ionic adduct $[TATP+^{14}NH_4]^+$. The second peak 408 represents the relative abundance of the ionic adduct $[TATP+^{15}NH_4]^+$. Peaks 406 and 408 are generated in a manner substantially similar to that for peaks 306, 308, 312, and 314 (all shown in FIG. 3).

Referring again to FIG. 2, as well as FIG. 3, as associated with performing 212 sample identification using comparative spectrometric data of the isotopes of the adduct ions, plot 400 may be representative of the real-time data imported into computing device 130 from data acquisition module 128 or historical spectrometric data resident in storage device 138 (all shown in FIG. 1).

In some embodiments, sample identification is performed 212 using comparative spectrometric data such as comparing ratios of associated isotopic adduct ions. In the exemplary embodiment, two ratio comparisons include comparing the values of relative peak intensity values (y-axis 402) of peaks 406 and 408 to each other and/or to historical data and comparing the isotopic peak areas defined by each of peaks 406 and 408 to each other and/or to historical data.

Similar results will be achieved using alternative molecular isotopes, including, without limitation, oxygen ($^{16}O$, $^{17}O$, and $^{18}O$), hydrogen ($^{1}H$ and $^{2}H$), carbon ($^{12}C$ and $^{13}C$), and potassium ($^{40}K$ and $^{41}K$).

Figure 5:
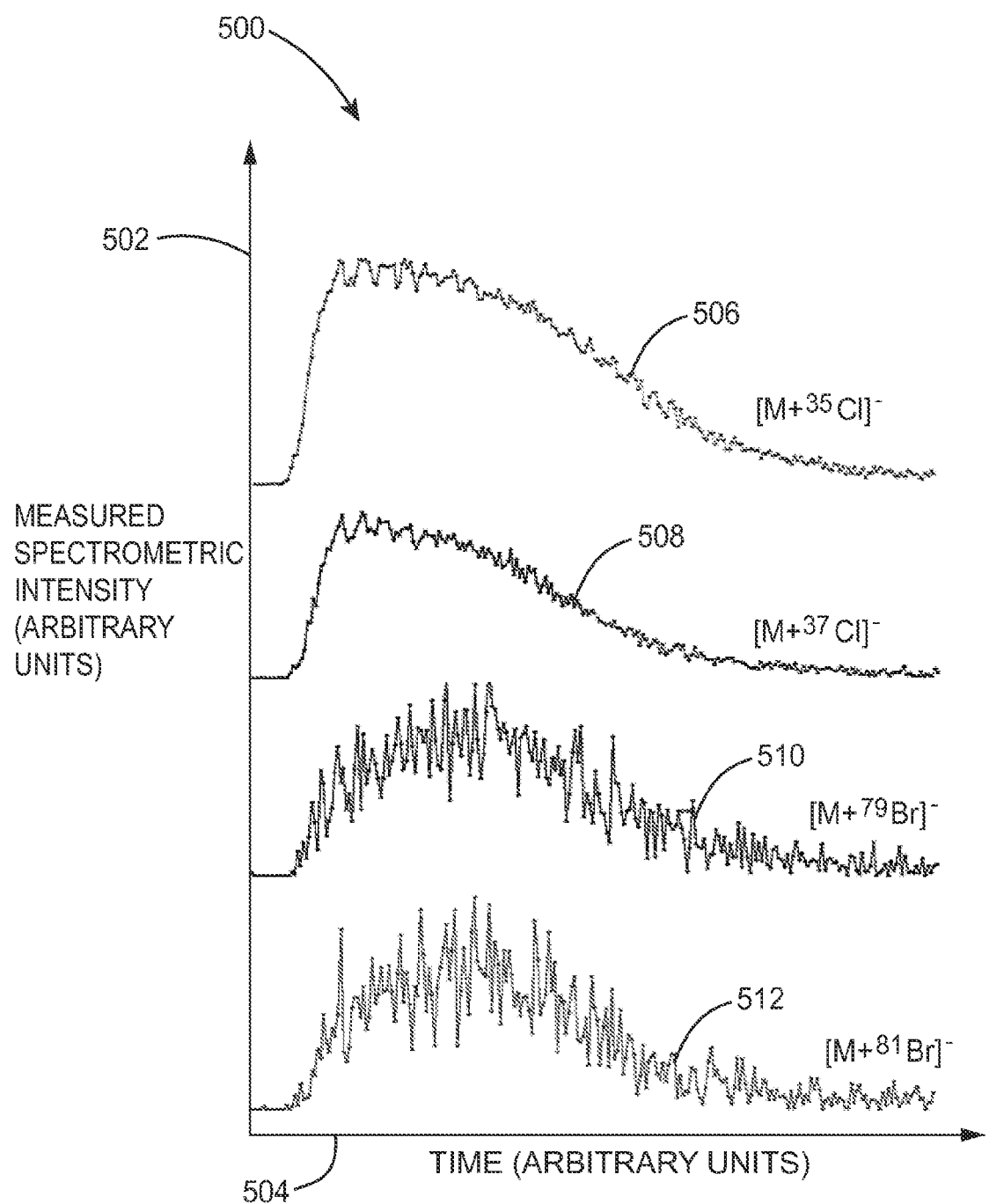

FIG. 5 is a graphical view, i.e., plot 500 of four thermal desorption profiles corresponding to $[NG+^{35,37}Cl]^-$ and $[NG+^{79,81}Br]^-$ adduct ions. Plot 500 includes a y-axis 502 representative of the relative abundances of the ionized molecules. Y-axis 502 is non-numerical to illustrate the approximate ionic abundances relative to each other. Plot 500 also includes an x-axis 504 representative of time in arbitrary units.

Sample introductions can include thermal desorption, chromatographic separation, or other means to separate the sample compounds. The time profiles are dependent on the properties of the compounds. Since properties of isotopic adducts differ very slightly for the different isotopes, the chemical properties of the sample compounds that they attach to are insignificantly affected. Therefore, adducts for different isotopes will show very similar time profiles by thermal desorption, chromatographic separation, or any other means of separating the sample molecules. This method can be used to determine if two observed peaks correspond to a single compound of interest or are due to different random background compounds.

In the exemplary embodiment, naturally-occurring $^{35}Cl^-$, $^{37}Cl^-$, $^{79}Br^-$, and $^{81}Br^-$ ion adducts are used. Plot 500 includes thermal desorption profiles for chloride adducts with compound M. Specifically, plot 500 includes a thermal desorption profile 506 for $[M+^{35}Cl]^-$ and a thermal desorption profile 708 for $[M+^{37}Cl]^-$ are formed. Similarly, plot 500 includes thermal desorption profiles for bromide adducts with compound M. Specifically, plot 500 includes a thermal desorption profile 510 for $[M+^{79}Br]^-$ and a thermal desorption profile 512 for $[M+^{81}Br]^-$. The similar shapes of curves 506, 508, 510, and 512 indicate that the two curves are due to a single compound M, i.e., NG.

Figure 6:
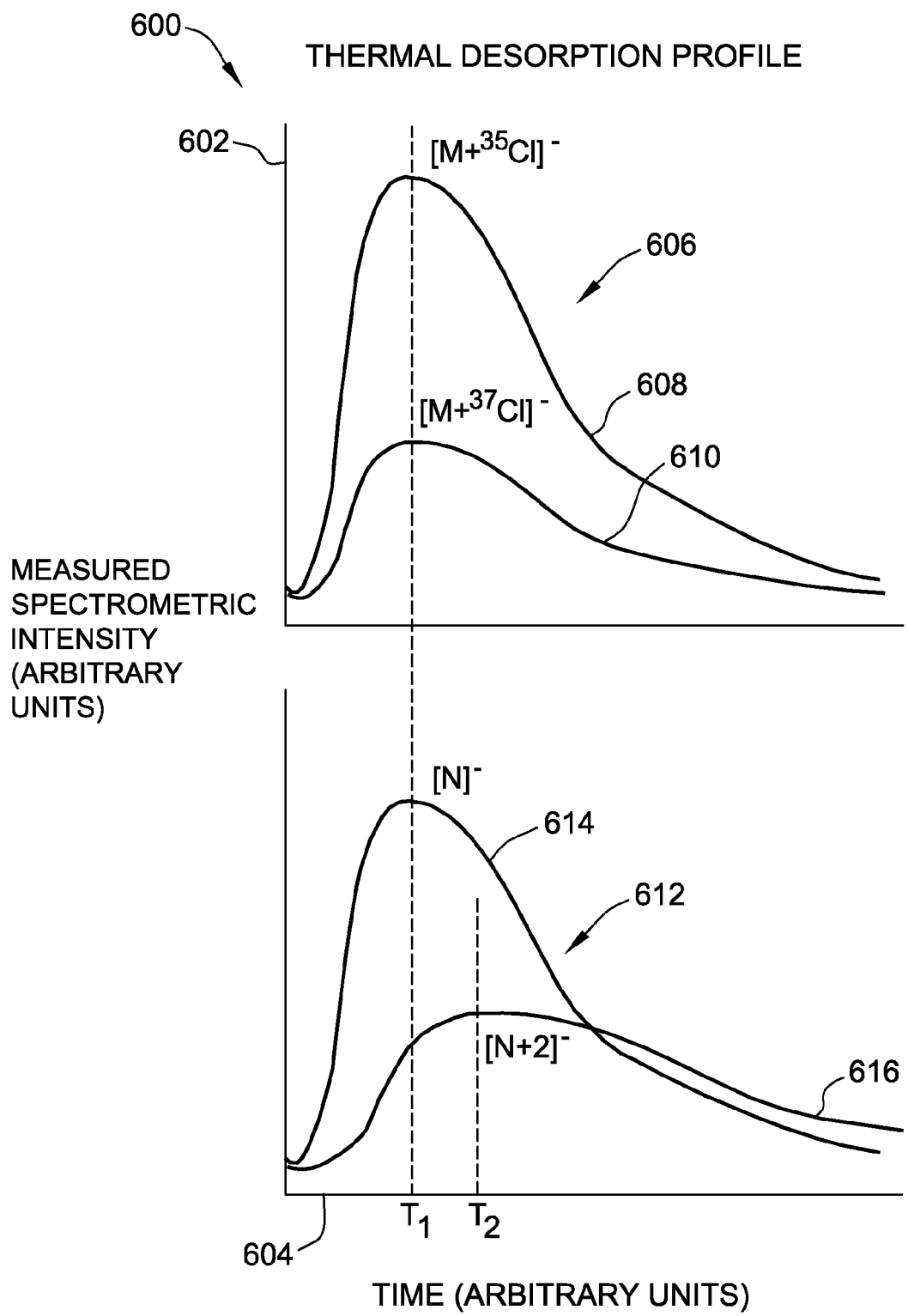

FIG. 6 is a graphical view, i.e., plot 600 of thermal desorption profiles corresponding to $[M+^{35,37}Cl]^-$ and other ionic compounds $[N]^-$ and $[N+2]^-$. Additional specificity is gained from the isotope distributions if the sample is introduced in a sequential, time dependent manner to processes in addition to that of spectrometric analysis device 124 (shown in FIG. 1).

Sample introductions can include thermal desorption, chromatographic separation, or other means to separate the sample compounds. The time profiles are dependent on the properties of the compounds. Since properties of isotopic adducts differ very slightly for the different isotopes, the chemical properties of the sample compounds that they attach to are insignificantly affected. Therefore, adducts for different isotopes will show very similar time profiles by thermal desorption, chromatographic separation, or any other means of separating the sample molecules. This method can be used to determine if two observed peaks correspond to a single compound of interest or are due to different random background compounds and is used to obtain the thermal desorption profiles shown in FIG. 6.

Plot 600 includes a y-axis 602 representative of the relative abundances of the ionized molecules. Y-axis 602 is non-numerical to illustrate the approximate ionic abundances relative to each other. Plot 600 also includes an x-axis 604 representative of time in arbitrary units.

In the exemplary embodiment, $^{35}Cl^-$ and $^{37}Cl^-$ isotopic chloride ion adducts are used. Plot 600 includes a thermal desorption profile 606 for chloride adducts with compound M, $[M+^{35}Cl]^-$ and $[M+^{37}Cl]^-$, i.e., curves 608 and 610, respectively. Because the thermal desorption properties of compound M are not affected by the isotopic differences for the chloride $Cl^-$ ion, the temporal profile will be the same as that described above using spectrometric analysis device 124 except for the ratio of intensity matching the isotopic distribution of $^{35,37}Cl^-$, i.e., in this case, a ratio of about 3:1 for $^{35}Cl^-$ and $^{37}Cl^-$, respectively. The similar shapes of curves 608 and 610 with the peaks at time $T_1$ indicates that the two peaks are due to a single compound M.

It is also possible that the two ion mass peaks may be due to two random other compounds, not necessarily of interest, that coincidently are in a ratio of 3:1. Without further analysis, this could cause a false positive response if there is no other information. However, such a possibility is detectable in thermal desorption plot 600 that includes a thermal desorption profile 612 of two ion masses separated by the isotopic difference of two mass units. Profile 612 includes curves 614 and 616 for compound $[N]^-$ and $[N+2]^-$ where the peak for curve 614 occurs at time $T_1$ and the peak for curve 616 occurs at time $T_2$. As such, curves 614 and 616 show that they are not due to the target compound M because the temporal profiles are different indicating that the two profiles 606 and 612 are due to two different compounds.

Figure 7:
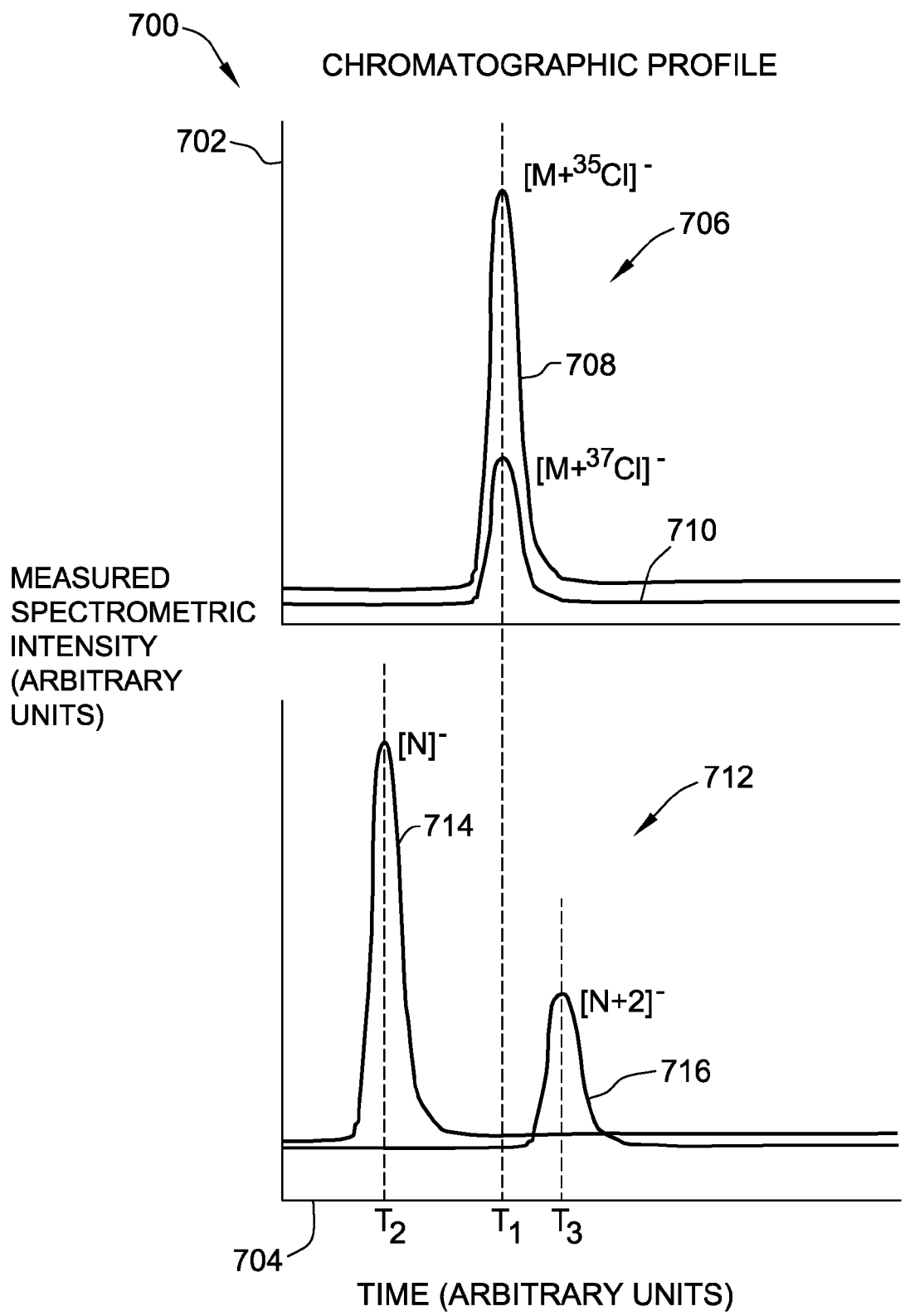

FIG. 7 is a graphical view, i.e., plot 700 of exemplary chromatographic profiles corresponding to $[M+^{35,37}Cl]^-$ and other ionic compounds $[N]^-$ and $[N+2]^-$. As described above for thermal desorption, a similar approach may be taken if thermal desorption is replaced/combined with chromatography techniques such gas, liquid, or ion exchange chromatography. Since isotope molecules bear very similar properties, elution profiles of molecular adduct ions with different isotopes should be nearly identical. Matching elution profiles adds an additional level of confidence in the identification procedures.

Plot 700 includes a y-axis 702 representative of the relative abundances of the ionized molecules. Y-axis 702 is non-numerical to illustrate the approximate ionic abundances relative to each other. Plot 700 also includes an x-axis 704 representative of time in arbitrary units.

The same considerations as that for thermal desorption described above apply to sample separation by chromatographic means. In the exemplary embodiment, $^{35}Cl^-$ and $^{37}Cl^-$ isotopic chloride ion adducts are used. Plot 700 includes a chromatographic profile 706 for chloride adducts with compound M, $[M+^{35}Cl]^-$ and $[M+^{37}Cl]^-$, i.e., curves 708 and 710, respectively. Because the chromatographic properties of compound M are not affected by the isotopic differences for the chloride $Cl^-$ ion, the temporal profile will be the same as that described above using thermal desorption, i.e., the different isotopes have the same chromatographic elution time. As such, the similar shapes of curves 708 and 710 with the peaks at time $T_1$ indicates that the two peaks are due to a single compound M.

It is also possible that the two ion mass peaks may be due to two random other compounds, not necessarily of interest, that coincidently are in a ratio of 3:1. Without further analysis, this could cause a false positive response if there is no other information. However, such a possibility is detectable in chromatographic plot 600 that includes a chromatographic profile 712 of two ion masses separated by the isotopic difference of two mass units. Profile 712 includes curves 714 and 716 for compound [N]⁻ and [N+2]⁻ where the peak for curve 714 occurs at time $T_2$ and the peak for curve 716 occurs at time $T_3$. As such, curves 714 and 716 show that they are not due to the target compound M because the temporal profiles, i.e., different chromatographic elution times are different indicating that the two profiles 706 and 712 are due to two different compounds.

The substance detection systems and methods described above enhance the specificity of trace detection systems through the use of additives having distinct isotopic patterns with a propensity to form predetermined adduct ions with substances of interest. Specifically, using compounds with known, naturally-occurring isotopic distributions increases the specificity of identification in a cost-effective manner. More specifically, the substance detection systems and methods described herein facilitate use of smaller, lighter, lower power intensive, and less expensive spectrometric analysis devices, e.g., single quadrupole mass spectrometry devices. Greater levels of specificity are attained if a mix of additives with different isotopic distributions is used. For example, use of chlorine and bromine together produce molecular ions with both chlorine and bromine adducts and each pair of ions have their own isotopic distribution. Furthermore, adduct ions are formed by attachment of a single additive molecular ion as well as multiple additive ions, for example, two isotopic chlorine ions or one ion each of isotopic chlorine and bromine. In such cases, the isotopic patterns are even more complex, and thus more distinctive. In addition, additives that produce ions other than adduct ions generate useful data on isotopic patterns, e.g., adducts may be formed with fragment ions of substances of interest or adduct ions may fall apart forming fragment adduct ions. Furthermore, rather than use naturally-occurring isotopic distributions, use of artificially isotopically-enriched compounds facilitates generating distinct isotopic patterns with even greater specificity.

An exemplary technical effect of the methods, systems, and apparatus described herein includes at least one of: (a) increasing the specificity of identification of substances of interest through the use of naturally-occurring isotopic distributions; (b) increasing the specificity of identification of substances of interest through the use of artificially isotopically-enriched compounds; and, (c) facilitating the use of smaller, lighter, lower power intensive, and less expensive spectrometric analysis devices, e.g., single quadrupole mass spectrometry devices.

Exemplary embodiments of substance detection systems for determining the presence of substances of interest, and methods of operating such systems are not limited to the specific embodiments described herein, but rather, components of systems and/or steps of the methods may be utilized independently and separately from other components and/or steps described herein. For example, the methods may also be used in combination with other systems requiring determining the presence of substances of interest, and are not limited to practice with only the substance detection systems and methods as described herein. Rather, the exemplary embodiment can be implemented and utilized in connection with many other substance detection applications that are currently configured to determine the presence of substances of interest.

Although specific features of various embodiments of the invention may be shown in some drawings and not in others, this is for convenience only. In accordance with the principles of the invention, any feature of a drawing may be referenced and/or claimed in combination with any feature of any other drawing.

Some embodiments involve the use of one or more electronic or computing devices. Such devices typically include a processor or controller, such as a general purpose central processing unit (CPU), a graphics processing unit (GPU), a microcontroller, a reduced instruction set computer (RISC) processor, an application specific integrated circuit (ASIC), a programmable logic circuit (PLC), and/or any other circuit or processor capable of executing the functions described herein. The methods described herein may be encoded as executable instructions embodied in a computer readable medium, including, without limitation, a storage device and/or a memory device. Such instructions, when executed by a processor, cause the processor to perform at least a portion of the methods described herein. The above examples are exemplary only, and thus are not intended to limit in any way the definition and/or meaning of the term processor.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for detecting a chemical substance, said method comprising:
   collecting a sample of a substance of interest;
   mixing the sample and at least one additive within a reaction chamber, wherein the at least one additive includes a plurality of isotopes;
   producing a plurality of adduct ions of the sample, the plurality of adduct ions having a plurality of isotopes;
   performing a spectrometric analysis of the plurality of isotopes of the plurality of adduct ions; and
   performing sample identification using comparative spectrometric data of the plurality of isotopes of the plurality of adduct ions, wherein the comparative spectrometric data includes data associated with ratios of a plurality of substantially similar isotopic ions.

2. The method according to claim 1, wherein mixing the sample of the substance of interest and at least one additive comprises using additive molecules having naturally-occurring isotopic compound distributions.

3. The method according to claim 2, wherein mixing the sample of the substance of interest and at least one additive comprises using an additive molecule that includes $^{37}Cl$ isotope.

4. The method according to claim 2, wherein mixing the sample of the substance of interest and at least one additive comprises using an additive molecule that includes $^{81}Br$ isotope.

5. The method according to claim 1, wherein mixing the sample of the substance of interest and at least one additive comprises using additive molecules having artificially isotopically-enriched compound distributions.

6. The method according to claim 5, wherein mixing the sample of the substance of interest and at least one additive comprises using an additive molecule that includes $^{15}$N isotope.

7. The method according to claim 5, wherein mixing the sample of the substance of interest and at least one additive comprises using an additive molecule that includes $^{17}$O isotope.

8. The method according to claim 5, wherein mixing the sample of the substance of interest and at least one additive comprises using an additive molecule that includes $^{18}$O isotope.

9. The method according to claim 5, wherein mixing the sample of the substance of interest and at least one additive comprises using an additive molecule that includes $^{2}$H isotope.

10. The method according to claim 5, wherein mixing the sample of the substance of interest and at least one additive comprises using an additive molecule that includes $^{41}$K isotope.

11. The method according to claim 5, wherein mixing the sample of the substance of interest and at least one additive comprises using an additive molecule that includes $^{13}$C isotope.

12. The method according to claim 5, wherein mixing the sample of the substance of interest and at least one additive comprises using an additive molecule that includes $^{37}$Cl isotope.

13. The method according to claim 5, wherein mixing the sample of the substance of interest and at least one additive comprises using an additive molecule that includes $^{81}$Br isotope.

14. The method in accordance with claim 1, wherein producing a plurality of adduct ions comprises producing adduct ions wherein:
    substantially all of the adduct ions have a negative polarity;
    substantially all of the adduct ions have a positive polarity; and
    there is a mix of adduct ions with a positive polarity and a negative polarity.

15. The method in accordance with claim 1, wherein performing a spectrometric analysis of the plurality of adduct ions comprises using mass spectrometry.

16. The method in accordance with claim 1, wherein performing a spectrometric analysis of the plurality of adduct ions comprises using ion mobility spectrometry.

17. The method in accordance with claim 16, wherein using ion mobility spectrometry comprises using differential ion mobility spectrometry.

18. The method in accordance with claim 1, wherein using data associated with ratios of a plurality of substantially similar isotopic adduct ions comprises comparing intensities of isotopic peaks of the plurality of isotopic adduct ions in a spectrum.

19. The method in accordance with claim 1, wherein using data associated with ratios of a plurality of substantially similar isotopic adduct ions comprises comparing intensities of isotopic peak areas of the plurality of isotopic adduct ions in a spectrum.

20. The method in accordance with claim 1, wherein using data associated with ratios of a plurality of substantially similar isotopic adduct ions comprises using data of isotopic ratios of molecular adduct ions.

21. The method in accordance with claim 1, wherein using data associated with ratios of a plurality of substantially similar isotopic adduct ions comprises using data of isotopic ratios of fragment adduct ions.

22. The method in accordance with claim 1, wherein performing sample identification using comparative spectrometric data of the isotopes of the plurality of isotopic adduct ions comprises using temporal profile data of elution profiles for isotopes of adduct ions.

23. The method in accordance with claim 22, wherein performing sample identification using comparative spectrometric data of the isotopes of the plurality of adduct ions comprises using temporal profile data of thermal desorption profiles for isotopes of adduct ions.

24. The method in accordance with claim 22, wherein performing sample identification using comparative spectrometric data of the isotopes of the plurality of adduct ions comprises using temporal profile data on chromatographic elution profiles for isotopes of adduct ions.

25. A substance detection system comprising:
    a reaction chamber housing defining a reaction chamber therein;
    a sample supply system coupled in flow communication with said reaction chamber, said sample supply system configured to channel at least a portion of a sample of interest to said reaction chamber;
    an additive system coupled in flow communication with said reaction chamber, said additive system configured to channel at least one additive to said reaction chamber, wherein the at least one additive includes a plurality of isotopes;
    an ionization source coupled in flow communication with said reaction chamber, said ionization source configured to produce a plurality of isotopic adduct ions from the at least a portion of the sample of interest and the at least one additive including the plurality of isotopes;
    a spectrometric analysis device coupled in flow communication with said reaction chamber, said spectrometric analysis device configured to perform a spectrometric analysis of the plurality of isotopic adduct ions; and
    a processor configured to identify at least one substance of interest using comparative spectrometric data of the plurality of isotopic adduct ions, wherein said comparative spectrometric data of the plurality of isotopic adduct ions comprises data associated with ratios of a plurality of substantially similar isotopic adduct ions, said processor is further configured to identify the at least one substance of interest using said data associated with ratios of a plurality of substantially similar isotopic adduct ions.

26. The system in accordance with claim 25, wherein said ionization source is configured to produce adduct ions having a polarity comprising one of:
    substantially all of the adduct ions have a negative polarity;
    substantially all of the adduct ions have a positive polarity; and
    there is a mix of adduct ions with a positive polarity and a negative polarity.

27. The system in accordance with claim 25, wherein said data associated with ratios of a plurality of substantially similar isotopic adduct ions comprises at least one of:
    intensities of isotopic peaks of the plurality of isotopic adduct ions in a spectrum;
    intensities of isotopic peak areas of the plurality of isotopic adduct ions in a spectrum;
    isotopic ratios of molecular adduct ions; and
    isotopic ratios of fragment adduct ions.

28. A method for detecting a chemical substance, said method comprising:
- collecting a sample of a substance of interest;
- mixing the sample and at least one additive within a reaction chamber, wherein the at least one additive includes a plurality of isotopes;
- producing a plurality of adduct ions of the sample, the plurality of adduct ions having a plurality of isotopes;
- performing a spectrometric analysis of the plurality of adduct ions; and
- performing sample identification using comparative spectrometric data of the plurality of isotopes of the plurality of adduct ions, wherein the comparative spectrometric data includes data associated with temporal profile data of the plurality of isotopes of the plurality of adduct ions.

* * * * *